(12) United States Patent
Akamatsu et al.

(10) Patent No.: US 8,563,618 B2
(45) Date of Patent: Oct. 22, 2013

(54) SKIN EXTERNAL PREPARATION HAVING EXCELLENT STABILITY

(75) Inventors: Hisashi Akamatsu, Yokohama (JP); Masashi Suzuki, Yokohama (JP); Yuji Sakai, Yokohama (JP)

(73) Assignees: Kuraray Co., Ltd., Okayama (JP); Pola Chemical Industries Inc., Shizuoka-shi, Shizuoka (JP)

( * ) Notice: Subject to any disclaimer, the term of this patent is extended or adjusted under 35 U.S.C. 154(b) by 803 days.

(21) Appl. No.: 12/305,356

(22) PCT Filed: Apr. 24, 2007

(86) PCT No.: PCT/JP2007/058775
§ 371 (c)(1),
(2), (4) Date: Dec. 17, 2008

(87) PCT Pub. No.: WO2007/148472
PCT Pub. Date: Dec. 27, 2007

(65) Prior Publication Data
US 2009/0181926 A1    Jul. 16, 2009

(30) Foreign Application Priority Data
Jun. 19, 2006   (JP) .................. 2006-169123

(51) Int. Cl.
*A61K 47/26*   (2006.01)
*A61K 47/10*   (2006.01)
*A61K 31/05*   (2006.01)
*A61K 31/734*   (2006.01)
*A61K 8/06*   (2006.01)

(52) U.S. Cl.
USPC .............. 514/779; 514/54; 514/731; 424/401

(58) Field of Classification Search
USPC .................. 514/54, 731, 779; 424/401
See application file for complete search history.

(56) References Cited

U.S. PATENT DOCUMENTS

| 6,132,740 | A | * | 10/2000 | Hu | 424/401 |
| 6,488,947 | B1 | * | 12/2002 | Bekele | 424/401 |
| 6,509,311 | B1 | * | 1/2003 | Colegrove | 512/4 |
| 2003/0152644 | A1 | * | 8/2003 | Modak et al. | 424/667 |

FOREIGN PATENT DOCUMENTS

| JP | 02-049715 | 2/1990 |
| JP | 07-149621 | 6/1995 |
| JP | 10-265332 | 10/1998 |
| JP | 2000-327557 | 11/2000 |
| JP | 2001-010925 | 1/2001 |
| JP | 2003-073281 | 3/2003 |
| JP | 2004-196728 | 7/2004 |
| JP | 2005-097123 | 4/2005 |

OTHER PUBLICATIONS

JPO machine translation of Japanese Patent Document JP 2000-327557, Japanese Patent Office AIPN, http://dossier1.ipdl.inpit.go.jp/AIPN/odse_top_dn.ipdl?N0000=7400, accessed online on Jun. 13, 2011.*
International Search Report dated Jun. 21, 2007.
Office Action issued on Dec. 10, 2010 to the corresponding Russian patent application No. 2009101325/15(001623).

* cited by examiner

*Primary Examiner* — Shaojia Anna Jiang
*Assistant Examiner* — Jonathan S Lau
(74) *Attorney, Agent, or Firm* — Knobbe, Martens, Olson & Bear LLP

(57) ABSTRACT

Disclosed is an agent for skin external preparation which is hardly reduced in viscosity even when stored for a long period under extreme high temperature storage conditions and is therefore stable. The preparation is in an emulsion form, and comprises (1) an alginic acid polyol ester having an esterification degree ranging from 75 to 95% (e.g., alginic acid propylene glycol ester) and/or a salt thereof; (2) a polyvalent metal ion (e.g., a calcium ion); and (3) a 4-alkylresolcinol (e.g., 4-n-butylresolcinol) and/or a salt thereof.

14 Claims, 2 Drawing Sheets

SKIN EXTERNAL PREPARATION HAVING EXCELLENT STABILITY

CROSS-REFERENCE TO RELATED APPLICATIONS

This application is the U.S. National Phase under 35 U.S.C. §371 of International Application PCT/JP2007/058775, filed Apr. 24, 2007, which was published in a non-English language, which claims priority to JP Application No. 2006-169123, filed Jun. 19, 2006.

TECHNICAL FIELD

The present invention relates to a skin external preparation in an emulsion form, and more specifically to a technology for improving storage stability under severe storage conditions.

BACKGROUND ART

An emulsified composition may contain both an oily component and an aqueous component, and hence being excellent as a skin external preparation. In general, an emulsion is prepared using a surfactant, but some of surfactants with low molecular weights may irritate the skin or may be partially decomposed to generate substances that irritate the skin (Patent Document 1). Therefore, there has been developed a technology for using a polymer compound having an emulsifying effect, such as an alkyl acrylate/methacrylate copolymer instead of the surfactant with a low molecular weight (Patent Documents 2 and 3). However, in the emulsifying technology using an alkyl acrylate/methacrylate copolymer, an emulsified composition is stabilized by ion repulsion of a carboxyl group, and hence, there may be a case where the pH varies with time during storage, and stability of the preparation deteriorates.

In view of such circumstances, an emulsified composition having both of safety and stability has been studied. For example, there has been developed an emulsified composition containing an alginic acid polyol ester, sodium alginate, and calcium chloride (Patent Document 4). The emulsified compositions are constantly stable under a certain temperature condition (40° C., about two weeks) to be employed in a general storage stability test for a cosmetic or the like.

However, in the case of the skin external preparation such as a cosmetic, the form of the preparation may change in some cases by long-term exposure to an unexpected severe high-temperature condition or the like during storage in distribution stage and at home, and the stability of the preparation is not enough yet.

Meanwhile, a 4-alkylresorcinol such as 4-n-butylresorcinol is known to have an effect of suppressing melanin production, and there is also known a technology for blending the substance in a skin external preparation to provide a skin-whitening effect (Patent Document 5, Non-Patent Document 1, etc.). In addition, there is known the fact that addition of a 4-alkylresorcinol and an unsaturated higher alcohol ether compound of a polyol can produce a stable emulsified composition (Patent Document 6) and a technology for obtaining an emulsified composition that is stable and has low viscosity by using an alkyl acrylate/methacrylate copolymer as an emulsifier (Patent Document 7).

On the other hand, it is not known that in an emulsified composition, which contains an alginic acid polyol ester such as alginic acid propylene glycol, a 4-alkylresorcinol can prevent a decrease in the viscosity of the composition, and a prescription using the compounds in combination has not been studied.

Patent Document 1: JP 07-149621 A
Patent Document 2: JP 10-265332 A
Patent Document 3: JP 2003-073281 A
Patent Document 4: JP 2004-196728 A
Patent Document 5: JP 02-49715 A
Patent Document 6: JP 2000-327557 A
Patent Document 7: JP 2001-10925 A
Non-Patent Document 1: Under the editorship of Takeda et al., "Usability of cosmetics, progress, and future prospect of evaluation technology", YAKUJI NIPPO LIMITED, published on Mar. 31, 2001

DISCLOSURE OF THE INVENTION

An object of the present invention is to provide a skin external preparation in an emulsion form, which is stable even when stored for a long period of time under a high-temperature condition.

In view of such circumstances, the inventors of the present invention have made extensive studies, and as a result, the inventors found out that addition of component (1) an alginic acid polyol ester having an esterification degree ranging from 75 to 95% and/or a salt thereof, component (2) a polyvalent metal ion, and component (3) a 4-alkylresorcinol and/or a salt thereof provides a skin external preparation which is hardly reduced in viscosity even when stored under severe storage conditions and has excellent stability, thus completing the present invention. That is, the present invention is as follows.

[1] A skin external preparation in an emulsion form including: component (1) an alginic acid polyol ester having an esterification degree ranging from 75 to 95% and/or a salt thereof; component (2) a polyvalent metal ion; and component (3) a 4-alkylresorcinol and/or a salt thereof.

[2] A skin external preparation according to the item [1], in which the component (3) is a 4-n-butylresorcinol and/or a salt thereof.

[3] A skin external preparation according to the item [1] or [2], in which the component (1) is an alginic acid propylene glycol ester having an esterification degree ranging from 75 to 95% and/or a salt thereof.

[4] A skin external preparation according to any one of the items [1] to [3] further including component (4) alginic acid and/or a salt thereof.

[5] A skin external preparation according to any one of the items [1] to [4] further including component (5) a dimer acid diester and/or a dimer diol diester.

[6] A skin external preparation according to the item [5], in which the component (5) di(phytosteryl/isostearyl/cetyl/stearyl/behenyl) dimer dilinoleate.

[7] A skin external preparation according to any one of the items [1] to [6], in which the skin external preparation is in an oil-in-water emulsion form.

[8] A skin external preparation according to any one of the items [1] to [7], in which the skin external preparation is a cosmetic.

BEST MODE FOR CARRYING OUT THE INVENTION

Figure 1:
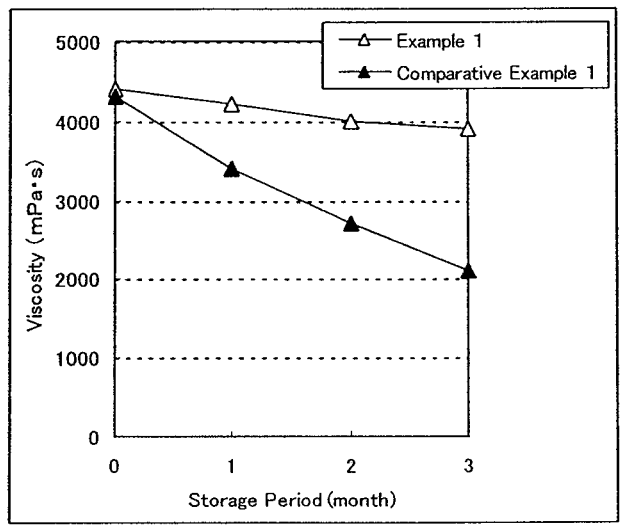
FIG. 1 A graph showing viscosity changes in Test Sample 2 stored under storage condition of 50° C.

<1> Alginic Acid Polyol Ester and/or Salt Thereof as Essential Component of Skin External Preparation of the Present Invention A skin external preparation of the present invention contains an alginic acid polyol ester having an esterification degree ranging from 75 to 95% and/or a salt thereof (component 1). Alginic acid constituting the alginic acid polyol ester is a heterogeneous linear polymer compound containing three blocks including a block of only β-D-mannuronic acid, a block of only α-L-guluronic acid, and a block of both of them. A polyol constituting the alginic acid polyol ester is not particularly limited as long as the polyol is used in a skin external preparation or the like. In particular, polyols having 2 to 4 carbon atoms are preferable. Specifically, preferable examples thereof include propylene glycol, glycerin, 1,3-butanediol, and ethylene glycol. Of those, propylene glycol is particularly preferable from the standpoint of the balance of hydrophilicity and hydrophobicity. The salt of the alginic acid polyol ester may be a salt obtained by substituting a monovalent cation for a hydrogen ion of a carboxyl group in an unesterified uronic acid residue of the alginic acid polyol ester, and in particular, preferable examples thereof include alkali metal salts such as sodium salts and potassium salts.

The esterification degree of the alginic acid polyol ester and/or the salt thereof to be used in the present invention ranges from 75 to 95% and may be appropriately selected depending on the type of a skin external preparation to be produced. In particular, in order to sufficiently form a cross-linking structure via a polyvalent metal ion described below, the esterification degree preferably ranges from 85 to 95%.

The viscosity of the alginic acid polyol ester and/or the salt thereof to be used in the present invention may be appropriately adjusted and selected depending on the type or the like of the skin external preparation to be produced. The viscosity at 20° C. in an aqueous solution containing the alginic acid polyol ester and/or the salt thereof at a concentration of 2% by mass is preferably 10 to 300 mPa·s, for example.

In addition, the preparation of the present invention may contain only one of the alginic acid polyol esters and salts thereof or may contain two or more of them. The content of the alginic acid polyol ester and/or the salt thereof may be appropriately adjusted depending on the type or the like of the skin external preparation. The content is preferably 0.1 to 5% by mass, more preferably 0.2 to 2% by mass, still more preferably 0.3 to 1% by mass with respect to the total amount of the skin external preparation. If the content is much lower than the ranges described above, the effect of the present invention may be hard to achieve in some cases, while if the content is much higher than the ranges described above, usability may be impaired in some cases.

The alginic acid polyol ester having an esterification degree ranging from 75 to 95% to be used in the present invention may be obtained by adding a carboxyl group of alginic acid to an epoxy compound such as propylene oxide or ethylene oxide at the same molar equivalent to that of the carboxyl group. Alternatively, the alginic acid polyol ester may be obtained by esterification through dehydration condensation of alginic acid and a polyol in accordance with a conventional method. Meanwhile, many of commercially available products of the alginic acid polyol esters have esterification degrees ranging from 75 to 95%, so the commercially available products may be used. Preferable examples of the commercially available products include "Kimiloid LLV", "Kimiloid NLS-K", "Kimiloid LV", "Kimiloid MV", "Kimiloid HV", and "Kimiloid BF", which are commercially available from Kimica Corporation. Of those, "Kimiloid BF" is particularly preferable.

<2> Polyvalent Metal Ion as Essential Component of Skin External Preparation of the Present Invention A skin external preparation of the present invention contains a polyvalent metal ion (component 2) in addition to the above-mentioned essential component. Examples of the polyvalent metal ions are not particularly limited as long as the polyvalent metal ions are those which are usually used in cosmetics and the like. Preferable examples thereof include a calcium ion, a magnesium ion, an aluminium ion, a zinc ion, a nickel ion, a copper ion, and an iron ion. Of those, the calcium ion, the aluminium ion, and the zinc ion are particularly preferable. Each of those polyvalent metal ions can bind to carboxylic acid in an unesterified uronic acid residue of an alginic acid polyol ester to form anionic cross-linkage with another uronic acid residue. A polyvalent metal ion can be added to the skin external preparation of the present invention in a state of polyvalent metal salt binding with a chloride ion, a sulfate ion, a nitrate ion, or the like.

The content of the polyvalent metal ion may be one which allows an alginic acid polyol ester having an esterification degree ranging from 75 to 95% and/or a salt thereof to be cross-linked sufficiently, and the content may be determined depending on the esterification degree of the alginic acid polyol ester or the type of the skin external preparation to be produced. In general, the content is preferably 0.001 to 1% by mass, more preferably 0.01 to 0.1% by mass with respect to the total amount of the preparation. Meanwhile, the content ratio of the polyvalent metal ion to the alginic acid polyol ester having an esterification degree ranging from 75 to 95% and/or the salt thereof may be appropriately adjusted in the same way as above. In general, the content ratio is preferably 0.005 to 0.5 times by mass, more preferably 0.01 to 0.1 times by mass with respect to the alginic acid polyol ester having an esterification degree ranging from 75 to 95% and/or the salt thereof.

<3> 4-Alkylresorcinol and/or Salt Thereof as Essential Component of Skin External Preparation of the Present Invention The skin external preparation of the present invention is characterized by containing a 4-alkylresorcinol and/or a salt thereof (component 3). The alkyl group in the 4-alkylresorcinol is preferably an alkyl group having 3 to 10 carbon atoms, more preferably an alkyl group having 3 to 6 carbon atoms. Specific examples of the alkyl group include n-propyl, isopropyl, n-butyl, isobutyl, sec-butyl, tert-butyl, amyl, n-hexyl, cyclohexyl, octyl, and isooctyl groups. The skin external preparation of the present invention particularly preferably contains 4-n-butylresorcinol. The 4-alkylresorcinol such as 4-n-butylresorcinol is a known substance and can be produced in accordance with a conventional method such as the method described in Lille, J.; Bitter, L. A.; Peiner, V. Trudy-Nauchono-Issledovatel' skii Institut Slantsev (1969), No. 18, 127-34. That is, examples of a method of producing 4-n-butylresorcinol includes: a method including condensing resorcin and butanoic acid in the presence of zinc chloride and reducing the resultant product with zinc amalgam/hydrochloric acid; and a method including condensing resorcin and n-butyl alcohol at 200 to 400° C. In this method, if another alcohol such as n-hexyl alcohol or cyclohexyl alcohol is substituted for n-butyl alcohol, another 4-alkylresorcinol such as 4-n-hexylresorcinol or 4-cycrohexylresorcinol can be synthesized. 4-n-hexylresorcinolis commercially available from Aldrich Chemical Company, Inc., and the product may be purchased and used.

In addition, the salts of 4-alkylresorcinol may be salts which are generally used in cosmetics and physiologically permitted. Examples of the salt preferably include salts of alkali metals such as sodium and potassium, salts of alkali earth metals such as calcium and magnesium, ammonium salts, salts of organic amines such as triethyl amine and triethanol amine, and salts of basic amino acid such as lysine and arginine.

The skin external preparation of the present invention may contain one of the 4-alkylresorcinols and salts thereof alone or may contain two or more of them in combination.

The content of the 4-alkylresorcinol or the like in the skin external preparation of the present invention is preferably 0.01 to 3% by mass, more preferably 0.05 to 1% by mass, further preferably 0.1 to 0.5% by mass in total with respect to the total amount of the preparation.

In addition, the content ratio of the 4-alkylresorcinol or the like is preferably 0.01 to 5 times by mass, more preferably 0.1 to 2 times by mass with respect to the alginic acid polyol ester having an esterification degree ranging from 75 to 95% and/or the salt thereof.

<4> Skin External Preparation of the Present Invention

A skin external preparation of the present invention contains: the alginic acid polyol ester having an esterification degree ranging from 75 to 95% and/or a salt thereof; the polyvalent metal ion; and the 4-alkylresorcinol, which are described above. The skin external preparation of the present invention is not particularly limited as long as the skin external preparation can be applied externally to the skin. Examples thereof include cosmetics (including quasi-drugs), pharmaceutical compositions for external application to skin, and miscellaneous products for external application to skin. Of those, cosmetics are particularly preferable. Note that in the case of using 4-n-butylresorcinol or the like, the preparation is more desirably applied to cosmetics, in particular, quasi-drugs.

The skin external preparation of the present invention is in the emulsion form, preferably in the form of an oil-in-water emulsion. Specifically, examples thereof include cream, skin milk, essence milk, and milk lotion.

The skin external preparation of the present invention preferably contains alginic acid and/or a salt thereof (component 4) in addition to the above-mentioned essential components. The compounds can further improve stability of the preparation. Note that alginic acid is as described above. The salt of alginic acid may be a salt obtained by substituting a monovalent cation for a hydrogen ion of a carboxyl group in an uronic acid residue, and preferable examples thereof include alkali metal salts such as sodium salts and potassium salts. The content of alginic acid and/or the salt thereof may be appropriately adjusted depending on the esterification degree, viscosity, and the like of the alginic acid polyol ester. In general, the content is preferably 0.1 to 2% by mass, more preferably 0.2 to 1% by mass with respect to the total amount of the preparation. The reason is that if the content is lower than the above ranges, the effect of the present invention may be hard to achieve in some cases, while if the content is higher than the above ranges, usability may be impaired in some cases because of high hardness of the preparation. Such alginic acid and salts thereof may be extracted from seaweed and the like or may be commercially available products. Examples of the products include sodium alginates such as "SKAT-ONE" (KIMICA Corporation), "SKAT-ULV" (KIMICA Corporation), "KIMICAALGIN I" (KIMICA Corporation), "KIMICA ALGIN ULV" (KIMICA Corporation), and those are also preferably used.

The skin external preparation of the present invention preferably contains a polar oil agent such as a dimer acid diester and/or a dimer diol diester (component 5) in addition to the above-mentioned essential components. The dimer acid diester can be obtained by esterifying a dimer acid with various alcohols in accordance with a conventional method. On the other hand, the dimer diol diester can be obtained by reducing a dimer acid to produce a dimer diol and esterifying the dimer diol with a fatty acid. Note that esters of the dimer acid and the dimer diol are also included in the concepts of both of the dimer acid diester and dimer diol diester.

The dimer acid is an aliphatic dibasic acid obtained by an intermolecular polymerization reaction of an unsaturated fatty acid. A dimer acid constituting the dimer acid diester of the present invention is preferably an aliphatic dibasic acid having 36 carbon atoms, which is a dimer of an unsaturated fatty acid having 18 carbon atoms. The dimer acid may be any of a compound having a cyclic structure in its molecule and a compound in which fatty acids bind to each other at one carbon atom of each fatty acid, or the dimer acid may be a mixture of two or more of them.

Industrial production methods for the dimer acids are almost standardized, and the dimer acids can be obtained by such methods. Polymerized products contain by-products such as monomer acids and trimer acids, and the polymerized products may contain the by-products, or may be purified by thin-film distillation or the like so as to have high purity. An unsaturated fatty acid constituting the dimer acid is not particularly limited as long as the unsaturated fatty acid can be used in safety for the skin external preparation. The unsaturated fatty acid is preferably an unsaturated fatty acid having 18 carbon atoms, particularly preferably oleic acid or linoleic acid derived from a plant such as soybean. The dimer acids are commercially available, and examples of a commercially available dimer dilinoleate include "Tsunodime" (TSUNO CO., LTD.). Such a commercially available product contains a dimer acid at a content of about 70 to 100% by mass. Such a product may be used without further treatment, or the product may be subjected to thin-film distillation or the like to increase the content ratio of the dimer acid and esterified or may be reduced to produce a dimer diol and esterified.

In the case where the dimer acid has unsaturated bonds, the dimer acid may be hydrogenated in all or a part of the unsaturated bonds to produce a hydrogenated product having partially or completely saturated bonds and esterified; or the dimer acid may be reduced to produce a dimer diol and esterified. In the present invention, such hydrogenated products of the dimer acids (hydrogenated dimer acids) are also in the concept of the dimer acids.

Preferred examples of the dimer diol obtained by reducing the dimer acid include dimer dilinoleyl alcohols and dimer dioleyl alcohols.

The alcohol to be used for obtaining a diester of the dimer acid is not particularly limited as long as the alcohol can be used in safety for the skin external preparation. Preferred examples thereof include higher alcohols and dimer diols obtained by reducing dimer acids. Examples of the higher alcohols include chain alcohols such as isostearyl alcohol, linoleyl alcohol, and behenyl alcohol, and aliphatic cyclic alcohols such as cholesterol and phytosterol. Examples of the dimer diols obtained through reduction of the dimer acids include dimer dilinoleyl alcohol and dimer dioleyl alcohol. In the dimer acid diester of the present invention, a diester using only one type of those alcohols may be used, or two or more types of alcohol diesters may also be used as a mixture.

The fatty acid to be used for obtaining the dimer diol diester is not particularly limited as long as the fatty acid can be used in safety for the skin external preparation. The skin external preparation is preferably a saturated or unsaturated fatty acid having 12 to 24-carbon atoms, more preferably a branched saturated fatty acid such as isostearic acid.

Examples of the dimer acid diester and the dimer diol diester used in skin external preparation of the present invention include di(phytosteryl/isostearyl/cetyl/stearyl/behenyl) dimer dilinoleate, di(isostearyl/phytosteryl) dimer dilinoleate, dimer dilinolic acid dimer dilinoleyl, and hydrogenated dimer dilinolic acid dimer dilinoleyl. Of those, di(phytosteryl/isostearyl/cetyl/stearyl/behenyl) dimer dilinoleate is particularly preferably used. The dimer acid diester and dimer diol diester may be commercially available products. Each of the commercially available products contains a dimer acid diester as a major component, and the content thereof is generally 70% by mass or more, preferably 90% by mass or more. Examples of the commercially available products include "Plandool-S", and "Plandool-H", manufactured by NIPPON FINE CHEMICAL CO., LTD., which are di(phytosteryl/isostearyl/cetyl/stearyl/behenyl) dimer dilinoleates, "LUSPLAN PI-DA", manufactured by NIPPON FINE CHEMICAL CO., LTD., which is a (isostearyl/phytosteryl) hydrogenated dimer dilinoleate, "LUSPLAN DD-DA5", manufactured by NIPPON FINE CHEMICAL CO., LTD. and "LUSPLAN DD-DA7", manufactured by NIPPON FINE CHEMICAL CO., LTD., which are hydrogenated dimer dilinolic acid dimer dilinoleyl, and "LUSPLAN DD-IS", manufactured by NIPPON FINE CHEMICAL CO., LTD., which is a diisostearic acid dimer dilinoleyl.

The skin external preparation of the present invention may contain one of the dimer acid diester and the dimer diol diester alone or may contain two or more of them in combination.

The content of the dimer acid diester and/or the dimer diol diester in the skin external preparation of the present invention is preferably 0.1 to 5% by mass, more preferably 0.5 to 2% by mass in total with respect to the total amount of the preparation.

The skin external preparation of the present invention can be used for the purposes of treatment, prevention, or amelioration of specific skin diseases or symptoms depending on various effects of an 4-alkylresorcinol or optional active ingredients. For example, the preparation is preferably a skin external preparation for anti-inflammation, suppression of melanin production, anti-bacteria, acne care, antioxidation, or skin-whitening; a cosmetic (including a quasi-drug) for prevention/amelioration of pigmentation; or the like, the preparation containing, for example, one or two or more selected from: anti-inflammatory agents such as vitamin E and/or a derivative thereof, glycyrrhizinic acid, and alkyl glycyrrhizinate and a salt thereof; and skin-whitening agents such as ascorbyl phosphate, ascorbyl glucoside, and kojic acid. Specifically, the skin external preparation is preferably a cosmetic such as a sun-care lotion or a sun-care milk, or a UV-protective basic skin care cosmetic, under make-up cosmetic, control color cosmetic, or foundation.

The skin external preparation of the present invention may further contain an optional component that is generally used in a skin external preparation. Such an optional component is not particularly limited as long as the component does not inhibit the effect of the present invention. Examples thereof include oils and waxes, hydrocarbons, higher fatty acid, higher alcohols, synthetic ester oils, lubricants, surfactants, polyols, moisturizing components, fine particles, inorganic pigments, organic dyes, organic fine particles, ultraviolet absorbents, lower alcohols, vitamins, antibacterial agents, thickeners, and various medicinal components. Those optional components may be blended in amounts not enough to inhibit the effect of the present invention.

Examples of the oils and waxes include macadamia nut oil, avocado oil, corn oil, olive oil, rapeseed oil, sesame oil, castor oil, safflower oil, cottonseed oil, jojoba oil, coconut oil, palm oil, liquid lanolin, cured coconut oil, cured oil, Japan wax, cured castor oil, beeswax, candelilla wax, carnauba wax, ibota wax, lanolin, reduced lanolin, hard lanolin, and jojoba wax.

Examples of the hydrocarbons include liquid paraffin, squalane, pristane, ozokerite, paraffin, ceresin, vaseline, and microcrystalline wax.

Examples of the higher fatty acids include oleic acid, isostearic acid, lauric acid, myristic acid, palmitic acid, stearic acid, behenic acid, and undecylenic acid.

Examples of the higher alcohols include cetyl alcohol, stearyl alcohol, isostearyl alcohol, behenyl alcohol, octyldodecanol, myristyl alcohol, and cetostearyl alcohol Examples of the synthetic ester oils include stearyl stearate, glyceryl triisostearate, cetyl isooctanoate, isopropyl myristate, hexyldecyl isostearate, diisopropyl adipate, di-2-ethylhexyl sebacate, cetyl lactate, diisostearyl malate, ethylene glycol di-2-ethyl hexanoate, neopentylglycol dicaprate, glycerin di-2-heptyl undacanoate, glycerin tri-2-ethylhexanoate, trimethylolpropane tri-2-ethylhexanoate, trimethylolpropane triisostearate, pentaerythritol tetra-2-ethylhexanoate, and N-acylglutamate dialkylesters.

Examples of the lubricants are silicone oil including chain polysiloxanes such as dimethylpolysiloxane, methylphenylpolysiloxane, and diphenylpolysiloxane; ring polyoxanes such as octamethylcyclotetrasiloxane, decamethylcyclopentasiloxane, and dodecamethylcyclohexanesiloxane; modified polysiloxanes such as amino-modified polysiloxane, polyether-modified polysiloxane, alkyl-modified polysiloxane, and fluorine-modified polysiloxane.

Examples of the surfactant include: anionic surfactants such as aliphatic soap (including sodium laurate and sodium palmitate), potassium lauryl sulfate, and triethanol amine ether alkyl sulfate; cationic surfactants such as chlorinated stearyl trimethyl ammonium, chlorinated benzalkonium, and lauryl amine oxide; and amphoteric surfactants such as imidazoline-based amphoteric surfactants (including 2-cocoyl-2-imidazolinium hydroxide-1-carboxyethyloxy-2-sodium salt), betaine-based surfactants (including alkyl betaine, amide betaine, and sulfobetaine), and acylmethyl taurine; nonionoic surfactants such as sorbitan aliphatic esters (including sorbitan monostearate, sorbitan sesquioleate, and sorbitan sesquistearate), glycerin aliphatic acids (including glycerinmonostearate), propylene glycol aliphatic esters (including propylene glycol monostearate), cured castor oil derivatives, glycerin alkyl ether, POE sorbitan aliphatic esters (including POE sorbitan monooleate and polyoxyethylene sorbitan monostearate), POE sorbit aliphatic esters (including POE-sorbit monolaurate), POE glycerin aliphatic esters (including POE-glycerin monoisostearate), POE aliphatic esters (including polyethyleneglycol monooleate and POE distearate), POE alkyl ethers (including POE 2-octyldodecyl ether), POE alkyl phenyl ethers (including POE nonylphenyl ether), Pluronic (registered mark), POE•POP alkyl ethers (including POE•POP 2-decyl tetradecyl ether), Tetronic (registered mark), POE castor oil-cured castor oil derivatives (including POE castor oil and POE cured castor oil), sucrose aliphatic esters, and alkyl glucoside.

Examples of the polyols include polyethylene glycol, glycerin, 1,3-butylene glycol, erythritol, sorbitol, xylitol, maltitol, propylene glycol, dipropylene glycol, diglycerin, isoprene glycol, 1,2-pentanediol, 2,4-hexanediol, 1,2-hexanediol, and 1,2-octanediol.

Examples of the moisturizing components include sodium pyrrolidone carboxylate, lactate, and sodium lactate.

Examples of the fine particles include mica, talc, kaolin, synthetic mica, calcium carbonate, magnesium carbonate, silicic anhydride (silica), aluminum oxide, and barium sulfate, whose surfaces may be treated.

Examples of the inorganic pigments include red iron oxide, yellow iron oxide, black iron oxide, cobalt oxide, ultramarine blue, iron blue, titanium oxide, zinc oxide, titanium mica, and bismuth oxychloride, whose surfaces may be treated.

Examples of the organic dyes include pearl agents such as fish scale foil, whose surfaces may be treated; and Red No. 202, Red No. 228, Red No. 226, Yellow No. 4, Blue No 404, Yellow No. 5, Red No. 505, Red No. 230, Red No. 223, Orange No. 201, Red No. 213, Yellow No. 204, Yellow No. 203, Blue No. 1, Green No. 201, Purple No. 201, and Red No. 204, which may be laked.

Examples of the organic fine particles include polyethylene powder, polymethyl methacrylate, nylon powder, and organopolysiloxane elastomer.

Examples of the ultraviolet absorbents include a p-aminobenzoate-based ultraviolet absorbent, an anthranilate-based ultraviolet absorbent, a salicylate-based ultraviolet absorbent, a cinnamate-based ultraviolet absorbent, a benzophenone-based ultraviolet absorbent, a sugar-based ultraviolet absorbent, 2-(2'-hydroxy-5'-t-octylphenyl)benzotriazole, and 4-methoxy-4'-t-butyldibenzoylmethane.

Examples of the lower alcohols include ethanol and isopropanol.

Examples of the vitamins include vitamin A or derivatives thereof, vitamin B types such as vitamin B6 hydrochloride, vitamin B6 tripalmitate, vitamin B6 dioctanoate, vitamin B2 or derivatives thereof, vitamin B12, and vitamin B15 or derivatives thereof, vitamin E types such as α-tocopherol, β-tocopherol, γ-tocopherol, and vitamin E acetate, vitamin D types, vitamin H, pantothenic acid, pantethine and pyrroloquinoline quinone.

Examples of the antibacterial agents include phenoxyethanol.

Examples of the thickeners include guar gum, quince seed, carageenan, galactan, gum arabic, pectin, mannan, starch, xanthan gum, curdlan, methyl cellulose, hydroxyethyl cellulose, carboxymethyl cellulose, methylhydroxypropyl cellulose, chondroitin sulfate, dermatan sulfate, glycogen, heparan sulfate, hyaluronic acid, sodium hyaluronate, tragacanth gum, keratan sulfate, chondroitin, mucoitin sulfate, hydroxyethyl guar gum, carboxymethyl guar gum, dextran, keratosulfate, locust bean gum, succinoglucan, charonin acid, chitin, chitosan, carboxymethyl chitin, agar, polyvinyl alcohol, polyvinyl pyrolidone, a carboxyvinyl polymer and/or salts thereof, an alkyl modified carboxyvinyl polymer and/or salts thereof, sodium polyacrylate, polyethylene glycol (PEG), and bentonite.

Examples of the various medicinal components include saponin of Centella asiatica, rosemary extract, white birch extract, and *Betula platyphylla* extract.

The skin external preparation of the present invention can be produced in accordance with a conventional method to be used for production of an emulsified composition. For example, in the case of production of the skin external preparation in the form of an oil-in-water emulsion, the preparation is preferably produced by the following method.

An oil-phase component and an oil-soluble optional component are added to an aqueous-phase component containing an alginic acid polyol ester having an esterification degree ranging from 75 to 95% and/or a salt thereof and a water-soluble optional component, and the mixture was stirred and emulsified. An aqueous solution of a polyvalent metal salt is further added thereto to form a cross-linking structure, resulting in stabilization of the emulsified composition. To the emulsified composition is finally added an aqueous solution of a 4-alkylresorcinol, to thereby obtain a skin external preparation. This method can disperse the 4-alkylresorcinol in the outer aqueous phase effectively and further improve stability of the preparation.

Hereinafter, the present invention will be described in more detail by way of Examples, but it is to be understood that the present invention is not limited to Examples.

EXAMPLES

Example 1

According to the following prescription, the components described in (A) were mixed and heated to 70° C., and a mixture of the components (B) heated to 70° C. was added thereto, followed by stirring using a homomixer to emulsify the mixture. A mixture of the components (C) heated to 70° C. was added thereto, and the whole was cooled with stirring. Then, a mixture of the components (D) was added there to at 40° C., and the whole was cooled to room temperature, to thereby prepare a cream as Example 1.

In Comparative Example 1, the same procedures as in Example 1 were repeated except that water was substituted for 4-n-butylresorcinol; in Comparative Example 2, the same procedures as in Example 1 were repeated except that water was substituted for calcium chloride; in Comparative Example 3, the same procedures as in Example 1 were repeated except that water was substituted for alginic acid propylene glycol; and in Comparative Example 4, the same procedures as in Example 1 were repeated except that water was substituted for both of 4-n-butylresorcinol and alginic acid propylene glycol.

(A)

| | |
|---|---|
| Propylene glycol alginate | 1.0 mass % |
| "Kimiloid BF" (50-175 mPa · S (2%), manufactured by Kimica Corporation) | |
| Sodium alginate | 0.5 mass % |
| "SKAT-ONE" (Manufactured by Kimica Corporation) | |
| 1,3-butanediol | 6.0 mass % |
| Glycerin | 5.0 mass % |
| Phenoxyethanol | 0.3 mass % |
| Pure water | 40.0 mass % |

(B)

| | |
|---|---|
| 2-ethylhexanoic acid triglyceride | 8.0 mass % |
| Isostearic acid | 1.0 mass % |
| Di(isostearyl/phytosteryl/cetyl/stearyl/behenyl) dimer dilinoleate "Plandool-H" (manufactured by NIPPON FINE CHEMICAL CO., LTD.) | 1.0 mass % |
| Tri(capryl/caprin/myristin/stearate) triglyceride "Saracos 334" (manufactured by THE NISSHIN OILLIO GROUP, LTD.) | 2.7 mass % |
| Behenyl alcohol | 0.3 mass % |
| Squalane | 1.0 mass % |
| Di(phytosteryl/2-octyldodecyl)N-lauroylglutamate "ELDEW PS-203" (manufactured by Ajinomoto Co., Inc.) | 0.5 mass % |
| Methylpolysiloxane (10 cs: centistokes, manufactured by Shin-Etsu Chemical Co., Ltd.) | 1.0 mass % |

(C)

| | |
|---|---|
| calcium chloride | 0.05 mass % |
| Pure water | 16.35 mass % |

(D)

| | |
|---|---|
| 4-n-butylresorcinol | 0.3 mass % |
| Pure water | 15.0 mass % |

Test Example 1

Stability Immediately after Preparation of Emulsion and During Short-Time-Storage (20° C. and 50° C., Overnight)

Glass containers (diameter 40 mmφ×height 120 mm) were separately filled with 100 ml of the samples, and the glass containers were covered and used as samples for measurement (two containers were used for each sample: container for 20° C. storage and container for 50° C. storage). The samples were stored overnight in a 20° C. temperature-controlled room and in a 50° C. temperature-controlled room, and observed.

In the case where each of the creams of Example 1 was stored at 20° C. and 50° C. overnight, both the creams were stable. As with the cream of Example 1, the cream of Comparative Example 1, obtained by substituting water for 4-n-butylresorcinol in the cream of Example 1, was stable when stored at 20° C. and 50° C. The cream of Comparative Example 2 remained in an emulsion state immediately after production of the cream, but the cream separated into two layers (oil phase and aqueous phase) after the cream was stored overnight at 20° C. and 50° C. The results reveal that a polyvalent metal ion such as calcium ion has an effect of stabilizing an emulsion. The creams of Comparative Examples 3 and 4 rapidly separated into two layers (oil phase and aqueous phase) immediately after production of the creams. The result reveals that it is impossible to produce an emulsion if a sample contains no alginic acid propylene glycol.

Those results reveal that presence of a polyvalent metal ion such as calcium ion is required to maintain an emulsion state during production although it is possible to produce an emulsion temporarily by emulsifying effect of an alginic acid polyol ester such as alginic acid propylene glycol. Based on those results, the creams of Example 1 and Comparative Example 1, which were confirmed to have short-time storage stability, were further subjected to a storage test under the severe condition.

Test Example 2

Long-Term Storage Test at High Temperature (50° C., 1 to 3 Months)

Next, the creams of Example 1 and Comparative Example 1, which were confirmed to have short-time storage stability in Test Example 1, were used to prepare samples in the same way as above (two containers were used for each sample: container for 20° C. storage and container for 50° C. storage). Those samples were stored overnight in a 20° C. temperature-controlled room and in a 50° C. temperature-controlled room, and the viscosities were measured. Measurement of the viscosities was performed using Vismetron viscometer (type VD) (Shibaura Systems Co., LTD.). Subsequently, the samples for 50° C. storage were stored overnight in the 20° C. temperature-controlled room, and the viscosities were measured again. After measurement of the viscosities, the samples for 50° C. storage were returned to the 50° C. temperature-controlled room and further stored. After one month, the viscosities of the samples for 20° C. storage, the viscosities of the samples for 50° C. storage, and the viscosities of the samples for 50° C. storage stored at 20° C. overnight were measured. In the same way as above, after a lapse of two and three months, the viscosities were measured. The results are shown below.

In the case where the creams were stored at 20° C. for three months, significant viscosity changes were not detected.

Figure 2:
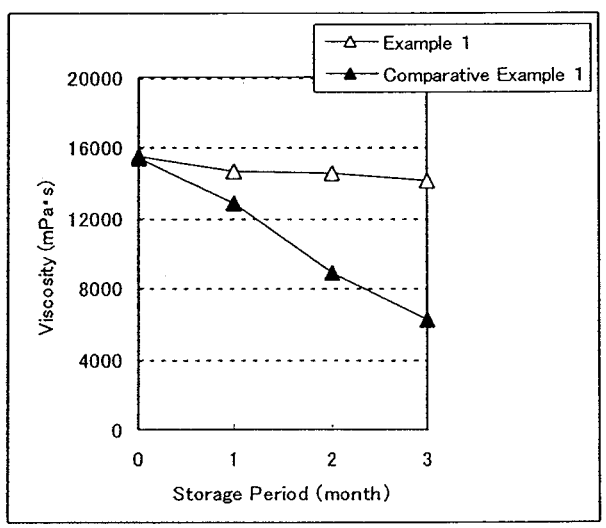
FIG. 2 A graph showing viscosity changes in Test Sample 2 in the case where the samples were stored at 50° C. and then returned to 20° C.

FIG. 1 shows the viscosity changes of the samples for 50° C. storage, and FIG. 2 shows the viscosity changes of the samples for 50° C. storage stored at 20° C. overnight.

As is clear from FIG. 1, even in the case where the cream of Example 1 containing 4-n-butylresorcinol was stored at 50° C., the viscosity change was small. On the other hand, in the case of the cream of Comparative Example 1 obtained by substituting water for 4-n-butylresorcinol, the viscosity was reduced with time, and after three month, the viscosity was reduced to about one-half of the viscosity of the cream immediately after production.

On the other hand, as is clear from FIG. 2, in the case where the creams were stored at 50° C. and then stored overnight at 20° C. in a temperature-controlled room, the viscosity of the cream of Example 1 recovered to the level of the cream immediately after production even after three months, while in the case of the cream of Comparative Example 1, the recovery degree of the viscosity was decreased with time. After a lapse of two months, the viscosity recovered to only about two-thirds of the viscosity of the cream immediately after production, and after a lapse of three months, the viscosity recovered to only about one-half of the viscosity of the cream immediately after production.

Further, the samples stored in the 50° C. temperature-controlled room for three months were stored in the 20° C. temperature-controlled room overnight, and the heights of oil phases in the samples were measured. The results are shown in Table 1.

TABLE 1

| | Height of oil phase (mm) |
|---|---|
| Example 1 | 0 |
| Comparative Example 1 | 1.0 |

The cream of Example 1 did not exhibit separation of an oil phase. On the other hand, the cream of Comparative Example 1 exhibited separation of a small amount of an oil phase.

Examples 2 to 4

According to the following prescription, a mixture of the components described in (B) heated to 70° C. was added to a mixture of the components described in (A) heated to 70° C., and the whole was stirred using a homomixer to emulsify the mixture, followed by addition of a mixture of the components described in (C) heated to 70° C. The resultant mixture was cooled with stirring, and the components described in (D) were added at 40° C., to thereby prepare a cream of Example 2. In Example 3, the same procedures as in Example 2 were repeated except that water was substituted for sodium alginate; in Example 4, the same procedures as in Example 2 were repeated except that water was added instead of removed "Plandool-H" at the same mass in the mixture of (D); and in Comparative Example 5, the same procedures as in Example 2 were repeated except that water was substituted for 4-n-butylresorcinol.

(A)

| | |
|---|---|
| Propylene glycol alginate "Kimiloid BF" (manufactured by Kimica Corporation) | 0.5 mass % |
| Sodium alginate | 0.5 mass % |
| 1,3-butanediol | 6.0 mass % |
| Glycerin | 5.0 mass % |
| Phenoxyethanol | 0.3 mass % |
| Pure water | 38.0 mass % |

(B)

| | |
|---|---|
| 2-ethylhexanoic acid triglyceride | 8.0 mass % |
| Isostearic acid | 1.0 mass % |
| Di(isostearyl/phytosteryl/cetyl/stearyl/behenyl) dimer dilinoleate "Plandool-H" (manufactured by NIPPON FINE CHEMICAL CO., LTD.) | 2.0 mass % |
| Tri(capryl/caprin/myristin/stearate) triglyceride "Saracos 334" (manufactured by THE NISSHIN OILLIO GROUP, LTD.) | 2.7 mass % |
| Behenyl alcohol | 0.3 mass % |
| Squalane | 1.0 mass % |
| Di(phytosteryl/behenyl/2-octyldodecyl)N-lauroylglutamate "ELDEW PS-304" (manufactured by Ajinomoto Co., Inc.) | 0.5 mass % |
| Methylpolysiloxane | 1.0 mass % |

(C)

| | |
|---|---|
| Calcium chloride | 0.05 mass % |
| Pure water | 17.85 mass % |

(D)

| | |
|---|---|
| 4-n-butylresorcinol | 0.3 mass % |
| Pure water | 15.0 mass % |

Test Example 3

Long-Term Storage Test at High Temperature (50° C., 1 to 3 Months)

In the same way as in Test Example 2, the creams of Examples 2 to 4 and Comparative Example 5 were subjected to 20° C. and 50° C. storage stability tests and viscosity recovery tests where the temperature was lowered from 50° C. to 20° C. The results are shown below.

In the case where the creams were stored at 20° C. for three months, significant viscosity changes were not observed in all the creams of Examples 2 to 4 and Comparative Example 5.

Figure 3:
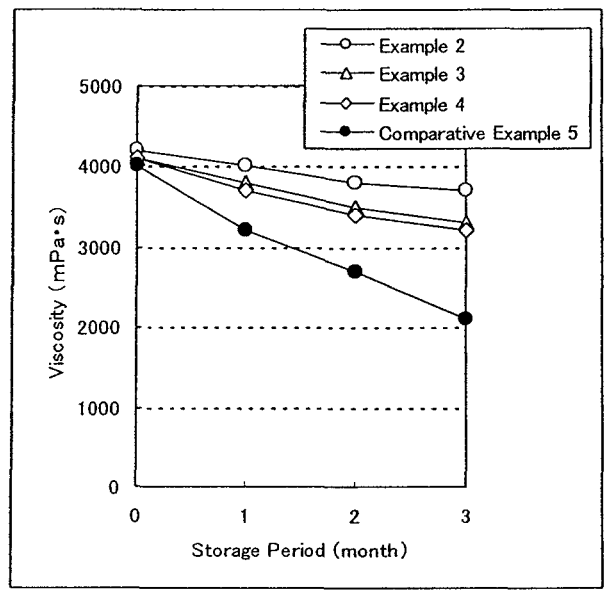
FIG. 3 A graph showing viscosity changes in Test Sample 3 under storage condition of 50° C.
Figure 4:
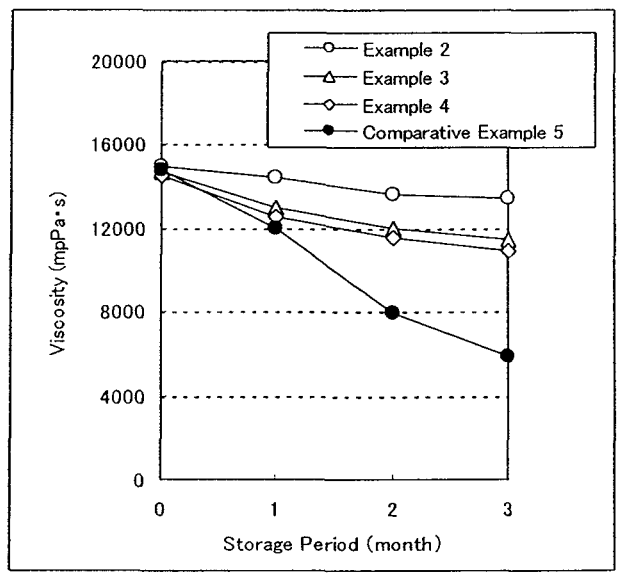
FIG. 4 A graph showing viscosity changes in Test Sample 3 in the case where samples were stored at 50° C. and then returned to 20° C.

FIG. 3 shows the viscosity changes of the samples for 50° C. storage, and FIG. 4 shows the viscosity changes of the samples for 50° C. storage stored at 20° C. overnight.

As is clear from FIG. 3, even in the case where the cream of Example 2 containing 4-n-butylresorcinol was stored at 50° C., the viscosity change was small. Meanwhile, in the cases of the creams of Examples 3 and 4, the viscosities were decreased in some degrees compared with the cream of Example 2. On the other hand, in the case of the cream of Comparative Example 5 obtained by substituting water for 4-n-butylresorcinol, the viscosity was decreased with time, and after a lapse of three months, the viscosity was decreased to about one-half of the viscosity of the cream immediately after production.

On the other hand, as is clear from FIG. 4, in the case where the cream of Example 2 was stored at 50° C. and then stored at 20° C. overnight in the temperature-controlled room, the viscosity recovered to the similar level of the cream immediately after production even after three months. Meanwhile, in the cases of the creams of Example 3 and 4, the recovery degree of the viscosity was slightly small compared with the cream of Example 2, but the viscosity recovered to the similar level of the viscosity of the cream immediately after production. Meanwhile, in the case of the cream of Comparative Example 5, the recovery degree of the viscosity was decreased with time, and after a lapse of three months, the viscosity recovered to only about one-half of the viscosity of the cream immediately after production.

The results reveal that alginic acid or diesters of dimer acid is not always required for suppression of a decrease in viscosity, but each of them can enhance an effect of suppressing a decrease in viscosity.

In addition, for the creams of Examples 2 to 4 and Comparative Example 5 stored for three months in the 50° C. temperature-controlled room, separation of the oil phase was observed in the same way as in Test Example 2. The results are shown in Table 2.

TABLE 2

| | Height of oil phase (mm) |
|---|---|
| Example 2 | 0 |
| Example 3 | 0 |
| Example 4 | 0 |
| Comparative Example 5 | 2.0 |

The creams of Examples 2 to 4 did not exhibit separation of the oil phase. On the other hand, the cream of Comparative Example 5 exhibited separation of a small amount of the oil phase.

The above-mentioned results reveal that use of an alginic acid polyol ester and a polyvalent metal ion as well as a 4-alkylresorcinol as components of the skin external preparation can achieve stable storage of the skin external preparation in an emulsion form for a long period of time of about one to three months.

INDUSTRIAL APPLICABILITY

Even if the skin external preparation in an emulsion form of the present invention is stored for a long period of time of about one to three months under an extremely-high-temperature condition, a decrease in the viscosity can be prevented without causing a change in its form such as separation. In addition, the preparation has very excellent storage stability because if the preparation is returned to room temperature after long-term storage under a severe condition, the viscosity can recover to the similar level of the viscosity of the cream immediately after production.

What is claimed is:

1. A skin external preparation in an emulsion form, comprising:
   component (1) an alginic acid polyol ester having an esterification degree ranging from 75 to 95% and/or a salt thereof in an amount 0.3-1% by mass with respect to the total amount of the preparation;
   component (2) a polyvalent metal ion; and
   component (3) a 4-alkylresorcinol and/or a salt thereof.

2. A skin external preparation according to claim 1, wherein component (3) is selected from the group consisting of 4-n-butylresorcinol, 4-n-hexylresorcinol, 4-cyclohexylresorcinol and salts thereof.

3. A skin external preparation according to claim 2, wherein component (1) is an alginic acid propylene glycol ester having an esterification degree ranging from 75 to 95% and/or a salt thereof.

4. A skin external preparation according to claim 2, further comprising component (4) alginic acid and/or a salt thereof.

5. A skin external preparation according to claim 2, wherein the skin external preparation is in an oil-in-water emulsion form.

6. A skin external preparation according to claim 2, wherein the skin external preparation is a cosmetic.

7. A skin external preparation according to claim 1, wherein component (1) is an alginic acid propylene glycol ester having an esterification degree ranging from 75 to 95% and/or a salt thereof.

8. A skin external preparation according to claim 7, further comprising component (4) alginic acid and/or a salt thereof.

9. A skin external preparation according to claim 7, wherein the skin external preparation is in an oil-in-water emulsion form.

10. A skin external preparation according to claim 7, wherein the skin external preparation is a cosmetic.

11. A skin external preparation according to claim 7, wherein component (3) is 4-n-butylresorcinol or a salt thereof.

12. A skin external preparation according to claim 1, further comprising component (4) alginic acid and/or a salt thereof.

13. A skin external preparation according to claim 1, wherein the skin external preparation is in an oil-in-water emulsion form.

14. A skin external preparation according to claim 1, wherein the skin external preparation is a cosmetic.

* * * * *